United States Patent

Berleth et al.

[11] Patent Number: 5,851,213
[45] Date of Patent: Dec. 22, 1998

[54] KNIFE HOLDER FOR A MICROTOME

[75] Inventors: Manfred Berleth, Eppelheim; Hans Heid, Bammental, both of Germany

[73] Assignee: Carl-Zeiss-Stiftung, Germany

[21] Appl. No.: 939,634

[22] Filed: Sep. 29, 1997

[30] Foreign Application Priority Data

Sep. 30, 1996 [DE] Germany .......................... 19640045.7

[51] Int. Cl.$^6$ .............................................. A61B 17/32
[52] U.S. Cl. .............................. 606/167; 83/67; 83/165; 83/915.5; 83/411.1
[58] Field of Search ........................... 606/167; 83/165, 83/915.5, 411.1

[56] References Cited

U.S. PATENT DOCUMENTS 3,704,557  12/1972  Peonski ................................ 51/165.75
5,065,657  11/1991  Pfeifer .................................. 83/703
5,148,729  9/1992  Krumdieck ........................... 83/411.1
5,226,335  7/1993  Sitte et al. ............................ 83/74

*Primary Examiner*—Michael Powell Buiz
*Assistant Examiner*—Vy Q. Bui

[57] ABSTRACT

A knife holder for a microtome has actuating levers for fastening or for releasing the knife on the knife holder, constructed such that in the position effecting the fastening of the knife, the actuating levers extend at least partially over the cutting edge of the knife. The actuating levers thereby act simultaneously as finger protectors and prevent inadvertent contact with the cutting edge in the side regions of the knife when the knife is fastened. The fastening of the knife takes place by means of permanent magnets, which are arranged in the base portion of the knife holder and motion-coupled to the actuating levers which cover the knife edge.

10 Claims, 2 Drawing Sheets

KNIFE HOLDER FOR A MICROTOME

BACKGROUND OF THE INVENTION

1. Field of the Invention

This invention relates to a knife holder for microtomes, and more particularly, to a knife holder for microtomes with interchangeable knives and blade holders for disposable blades.

2. Discussion of Prior Art

In known knife holders for microtomes, the interchangeable knife, or the blade holder for disposable blades, is mechanically, fixedly clamped between a base portion of the knife holder and a clamping plate. An eccentric shaft, operated by means of a lever, is provided for the clamping motion between the base portion and the clamping plate of the knife holder. Such knife holders are known, for example, from German Patent C2 35 40 861 or from U.S. Pat. No. 4,700,600. In order to fix the knife or the blade holder in the correct position before the clamping proper, weak permanent magnets can be provided, which are set with adhesive in recesses in the seating surface for the knife or the blade holder.

In these known knife holders, the clamping plate has frequently proved to be troublesome when removing the sections, since the back surface of the knife is not freely accessible for placing a slide for removal of a section. Furthermore, the insertion and removal of the knife is complicated, since the knife has to be pushed in either from the side or from above into the slot which remains between the base portion and the clamping plate.

Furthermore, knife holders usually have a so-called finger protector. Such a finger protector can consist of a U-shaped lever which is pivotably jointed to the base body of the knife holder. The portion of the finger protector that connects the two U-shanks extends in an end position above the blade of the knife and thus prevents an inadvertent hand contact with the cutting edge of the knife.

SUMMARY OF THE INVENTION

The present invention has as its object a knife holder for microtomes, in which the operating convenience of the knife holder is improved over known knife holders.

This object is attained according to the invention by a knife holder for a microtome having a knife or a blade holder for a blade, to be received by the knife holder, and at least one actuating lever that is arranged, upon actuation, to fasten the knife or blade holder. The actuating lever includes an extension that extends at least partially over a cutting edge of the knife or the blade. As a further advantageous feature according to the invention, at least one magnet is provided in a base portion of the knife holder for fastening the knife or the blade holder, in which movement of the actuating lever effects movement of the magnet.

In an embodiment of the knife holder according to the invention, the actuating lever that is operated for fastening the knife acts at the same time as a finger protector, so that when the knife or blade holder is fastened, the hands are protected from inadvertent contact with at least a portion of the knife blade. After a knife change or a change of the location which is in use on the knife blade, a portion of the knife blade is thus constantly covered with the simplest of means, without an additional actuating element having to be operated.

In an additional embodiment of the invention, the fastening of the knife or the blade carrier takes place by magnets which are inset into the base portion of the knife carrier and, on actuation of an actuating lever, are moved so that the magnetic force in one position of the actuating lever reliably holds the knife or the blade holder firmly on the knife carrier, and in another position of the lever releases the knife or the blade carrier to the extent that easy displaceability of the knife is insured. The magnet or magnets can be received for this purpose in the base portion, movably in a direction at right angles to the seating surface for the knife. For conversion of the motion of the actuating lever into the linear movement of the magnet or magnets, an eccentric shaft is provided which is rotatably mounted in the base body of the knife holder and which extends through slotted holes in the magnets or in the carriers for the magnets. The eccentrics for the eccentric shaft can then be provided at the places corresponding to the slotted holes.

Holding the knife or the blade holder to the knife carrier by means of magnetic force gives the advantage, over the otherwise usual mechanical clamping, that no additional clamping plates are required. The back side of the knife or blade holder is thereby freely accessible for removal of a section. The insertion and removal of the knife or of a blade holder can take place easily from above, in that they are only placed flat on the base portion; pushing them into a gap is not required. Furthermore, the knife carrier which is free from clamping plates affords a greater freedom of design and in the use of blade holders, since the thickness of the blade holder does not need to be determined by the usual knife thickness. Finally, the otherwise frequent need to change the clamping plate, which is shaped to match the thickness and wedge angle of the knife or blade holder being used, no longer arises when changing between knives of different thickness or wedge angle.

An advantageous embodiment of the invention has the features of both embodiments in combination, that is, the actuating lever or levers, which actuate the motion of the magnet into the position in which fastening of the knife or blade holder is affected, extend at least partially over the knife blade.

In a further advantageous embodiment of the invention, two actuating levers, which are movable independently of each other, are provided at the two opposed ends of the knife carrier. Then the hands are protected against inadvertent contact with the knife blade in both the left-hand edge region of the knife and the right-hand edge region of the knife only the central region of the knife, used for the production of sections during operation of the microtome, remains without protection. The region of the knife blade which lies free is thereby of constantly equal size when the knife is fastened, independently of the knife length. Thus, even the use of longer knives leads to no increase in the risk of injury in comparison with the use of shorter knives.

The two actuating levers which extend over the knife blade or blade edge can thus be mounted independently of each other and can be coupled, as regards motion, to different magnets. In particular, two or more magnets can also be coupled to the motion of each of the two levers, so that even knives of different lengths can be held securely on the knife carrier.

BRIEF DESCRIPTION OF THE DRAWINGS

Details of the invention are described more fully hereinbelow with reference to the preferred embodiment, taken together with the drawings, in which.

DETAILED DESCRIPTION OF PREFERRED EMBODIMENTS

Figure 1:
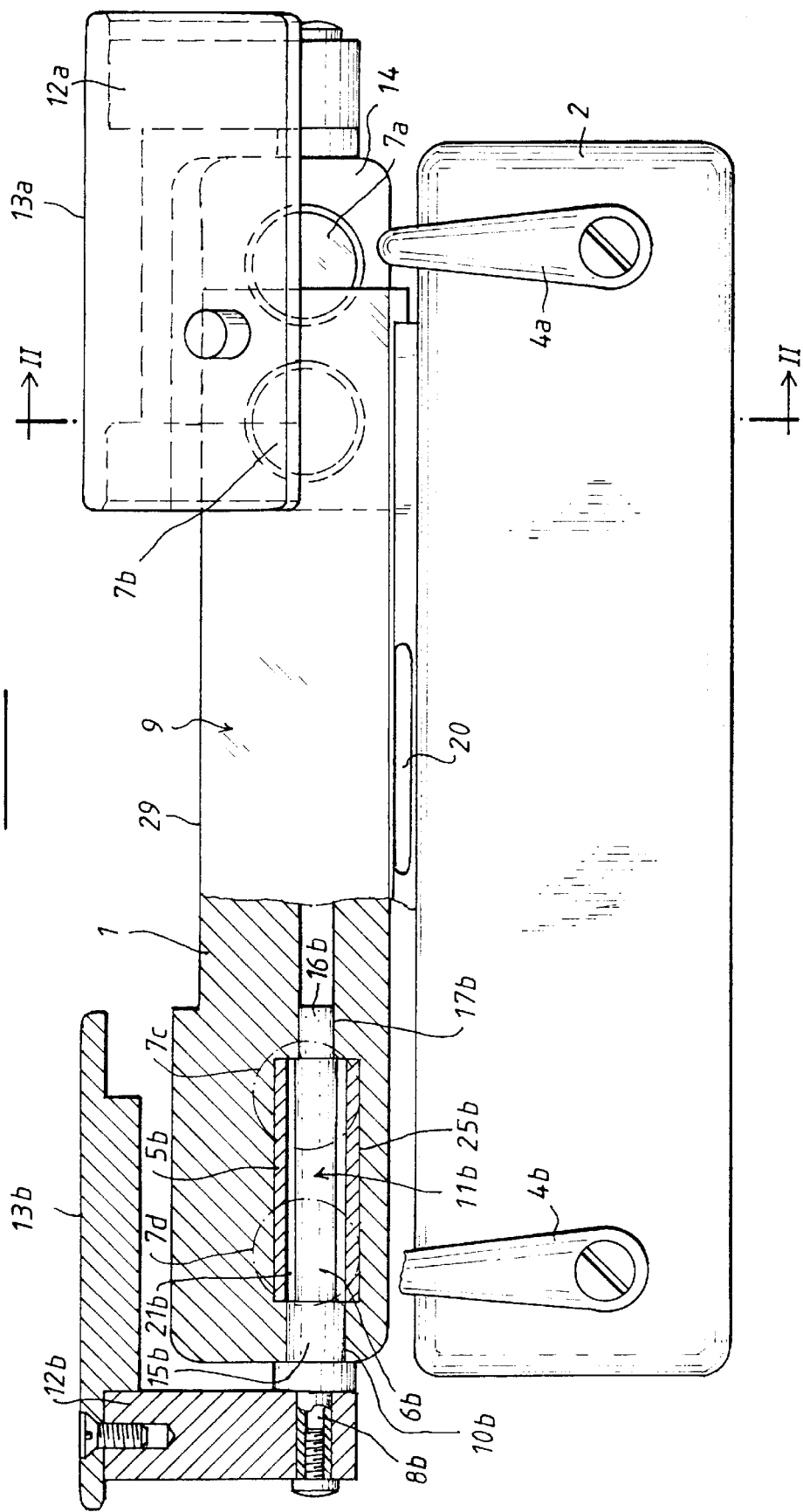
FIG. 1 shows a plan view of a knife carrier according to the invention, with a cutting knife received on it, in partial section.

The knife carrier according to the invention contains a base portion (1), the cylindrical back surface of which is pivotably received, in a known manner, on a receiving portion (2) fastened to the microtome. The so-called setting angle of the knife, and thus the orientation of the knife edge (29) relative to the sample to be sectioned, can be varied by pivoting the base portion (1) along the cylindrical back surface. In order to secure a position, once set, between the base portion (1) and the receiving portion (2), a known eccentric clamping by means of an eccentric shaft (3a, 3b) and an operating lever (4a, 4b) is provided.

Figure 3:
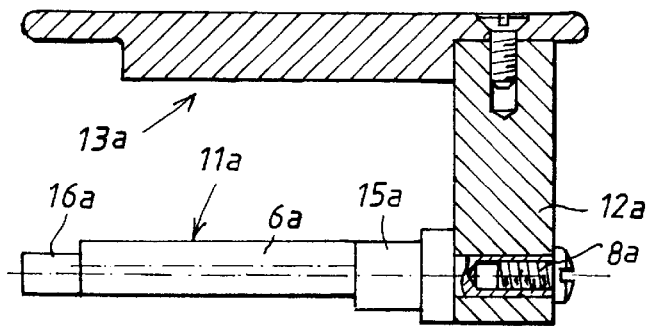
FIG. 3 shows a section through an actuating lever of the knife carrier according to FIG. 1.

The base portion (1) has on the upper side several milled recesses (25a, 25b), into which receiving bodies (5a, 5b) for strong permanent magnets (7a–7d) are inserted. The receiving bodies (5a, 5b) each have a slotted hole (21a, 21b) in the longitudinal direction of the base portion (1), i.e., parallel to the cutting edge (29) of the knife (9) which is to be received. Two coaxial bores (10b, 17b) are provided on each side of the base portion (1), and the respective sections (15a, 16a or 15b, 16b) of the eccentric shafts (11a, 11b) are mounted in them (see also FIG. 3). The eccentrics (6a, 6b), arranged eccentrically of the sections (15a, 16a or 15b, 16b) of the eccentric shafts (11a, 11b), serve to move the receiving bodies (5a, 5b) and thus to move the magnets (7a–7d), in order to fix the knife (9) in the set position or to release it. The actuation of the eccentric shafts (11a, 11b) then takes place by means of two actuating levers (12a, 12b), located at the two ends of the base portion (1) and connected to the eccentric shafts (11a, 11b). The two actuating levers (12a, 12b) each have an extension (13a, 13b) which extends in the longitudinal direction of the base portion (1) and which is constructed as a segment of a cylindrical shell. The actuating levers, including the extensions, thereby have a L-shaped cross section. The function of one actuating lever (12a) is to move two permanent magnets (7a, 7b) on the one side of the base portion (1), and the function of the second actuating lever (12b) is to move the two permanent magnets (7c, 7d) arranged on the other side of the base portion (1).

Figure 2:
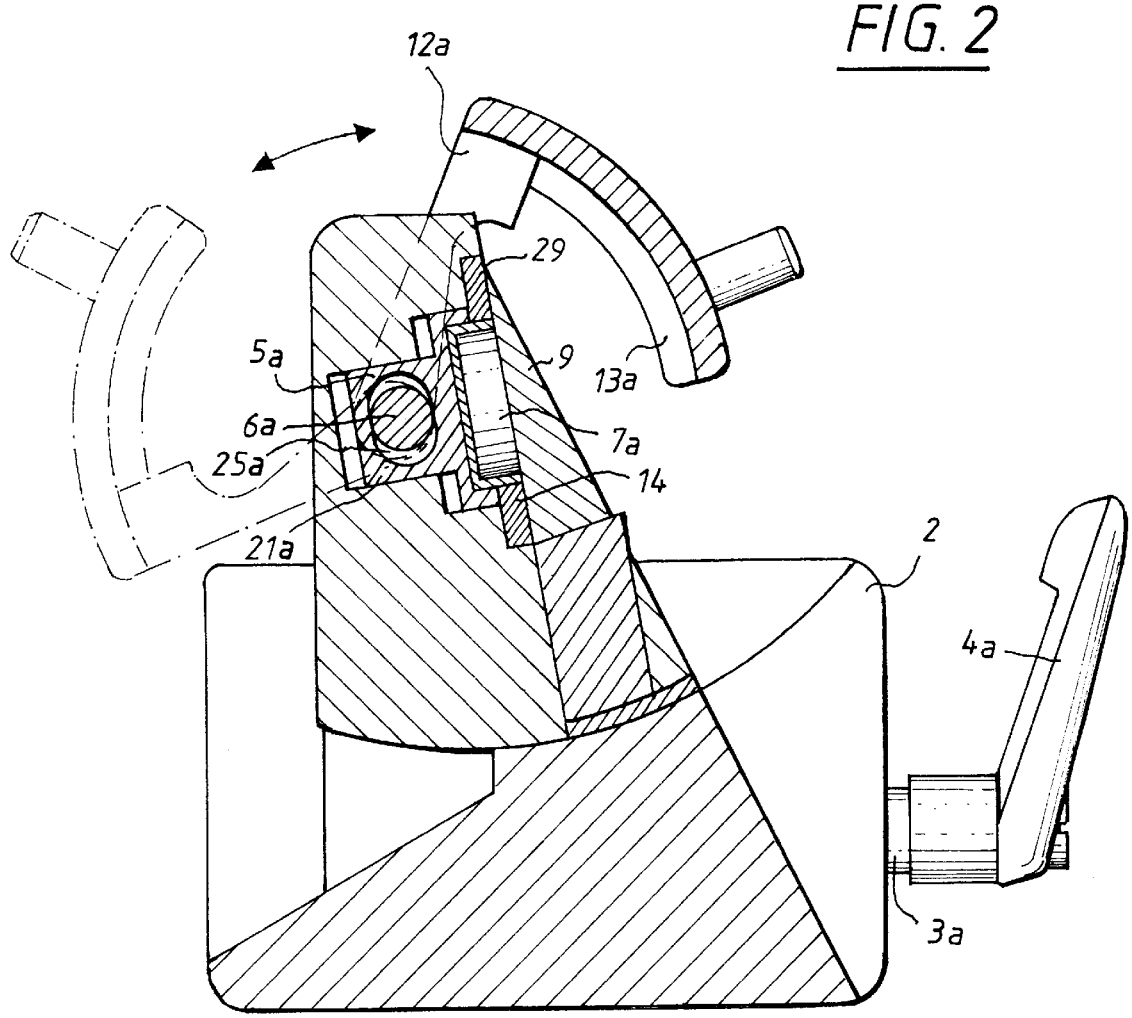
FIG. 2 shows a section through the knife carrier of FIG. 1, along the line II—II.

As can be seen in particular from FIG. 2, the upper side of the base portion (1) is partially covered by a plate (14) of non-ferromagnetic material, e.g., brass, which has holes at the positions corresponding to the permanent magnets (7a–7d), and the surface of which is flush with the surface of the permanent magnets. This plate (14) serves as a seating surface for the knife (9). Since the permanent magnets (7a–7d) have a smaller diameter than the receiving bodies (5a, 5b) for the permanent magnets, the cover plate (14) serves at the same time to hold the permanent magnets (7a–7d) and the associated receiving bodies (5a, 5b) within the milled recesses of the base portion (1).

In the position of the actuating lever 12a shown dashed in FIG. 2, the two permanent magnets (7a, 7b) together with their receiving body (5a) are displaced by 1–2 millimeters into the interior of the base portion (1). An air gap thereby arises between the permanent magnets (7a, 7b) and the knife (9), so that the magnetic force exerted by the permanent magnets (7a, 7b) on the knife (9) greatly decreases. The same is true for the permanent magnets (7c, 7d) for a corresponding pivoting position of the second actuating lever (12b, 13b). In this case, the knife (9) is easily displaceable on the plate (14); at the same time, there still remains a residual magnetic force, by which the knife (9) is held by a small force and is prevented from falling out. When the actuating levers (12a, 13a) are pivoted into the position shown by solid lines in FIG. 2, the magnets (7a, 7b) are directly moved, as far as the base surface of the knife (9). The knife (9) is held fast to the plate (14) of the knife carrier by the then substantially stronger magnetic force between the permanent magnets (7a, 7b) and the knife (9), and is fixed in its position relative to the seating surface formed by the cover plates (14). In this second pivoting position of the actuating levers (12a, 13a), the extension (13a), formed as a segment of a cylindrical shell, of the lever (12a) extends over the edge regions of the cutting knife (9) along the knife edge (29), and covers the portions of the knife which have the cutting edge (29) in this edge region. Protection is thereby provided in these edge regions against inadvertent contact with the knife edge (29).

As is shown in FIG. 1, two permanent magnets (7a, 7b) or (7c, 7d) are provided on each long side of the base portion (1). Each of these permanent magnets (7a–7d) is set up, with respect to its magnetic force, such that the force exerted on the knife (9) by two respective permanent magnets is sufficient to hold the knife (9) in the respective position even during the cutting of the section. Therefore the knife (9), whose length is shorter than the length of the base portion (1), can be fastened in the different positions on the knife carrier, so that different regions of the knife (9) can be used for cutting. If the cutting edge (29) of the knife (9) is blunted in a region, it is only necessary to release the fastening, displace the knife parallel to the cutting edge (29), and fasten it again.

In the embodiment shown in FIG. 1, the base portion (1) has an opening (20) in the rear region, and thus in the region in which the base portion is received on the receiving portion (2). This opening (20) serves for sucking away cutting waste, and corresponds to a further bore (not shown here in detail) through the receiving portion (2) and having a diameter which is designed such that a connection to the opening (20) is insured, even in the different pivoting positions of the base portion (1), relative to the receiving portion (2). The bore (not shown) is connected in a known manner to a suction pump and a trap container for the cutting waste.

The knife holder according to the invention can be used both to receive microtome knives, which are relatively thicker and are resharpenable, and usually consist of magnetic material, and disposable blades. When disposable blades are used, which are usually very thin and do not inherently have sufficient stability, they are received in a blade holder of magnetic material, and the blade holder, with the disposable blade received in it, is then fixed to the knife holder by the magnetic force of the permanent magnets (7a–7d).

In order to also insure a finger protection in the middle region of the knife edge when a microtome with a knife holder according to the invention is stationary, a yoke which can be folded over the middle portion of the cutting edge is provided on the base portion or on a cut extender received on the base portion. The pivoting back and forth of this yoke requires, however, an additional operating step.

In the embodiment shown in the Figures, two eccentric shafts (11a, 11b) are provided, so that the movement, and the "switching on and off" of the permanent magnets (7a, 7b) and of the two other permanent magnets (7c, 7d) takes place independently of each other. Alternatively, a single eccentric shaft, passed through the base portion, could be provided, so that the movement of the two actuating levers (12a, 13a and 12b, 13b) is coupled together. The movement of the two actuating levers (12a, 13a and 12b, 13b) then respectively takes place simultaneously, all the permanent magnets (7a–7d) likewise being moved forward or backward simultaneously.

In the described embodiments, the extensions (13a, 13b) which extend over the cutting edge are constructed as cylindrical envelope segments. Alternatively, extensions of other shapes are possible, e.g., curved or angled metal sheets. Moreover handles for actuating the levers can also be provided on the extensions.

We claim:

1. A knife holder for holding a knife or a blade holder for a blade of a microtome, comprising:

at least one actuating lever (12a, 12b) that is arranged, upon actuation, to fasten said knife or blade holder, wherein said actuating lever (12a, 12b) includes an extension (13a, 13b) that extends at least partially over a cutting edge (29) of said knife or said blade.

2. The knife holder according to claim 1, comprising two actuating levers pivotable independently of each other.

3. The knife holder according to claim 1, wherein a portion of said at least one actuating lever (13a, 13b) extends parallel to said cutting edge (29) of said knife or said blade and is in a form of a segment of a cylindrical shell.

4. The knife holder according to claim 1, wherein a portion of said at least one actuating lever (13a, 13b) extends parallel to said cutting edge (29) of said knife or said blade and is movable to cover over said cutting edge (29).

5. A knife holder for a microtome, comprising:

a knife or a blade holder for a blade, to be received by said knife holder, at least one actuating lever that is arranged, upon actuation, to fasten said knife or said blade holder, and at least one magnet (7a, 7b) provided in a base portion (1) of said knife holder for fastening said knife or said blade holder, wherein movement of said actuating lever (12a, 12b) effects movement of said at least one magnet (7a, 7b).

6. The knife holder according to claim 5, wherein said at least one magnet (7a, 7b) is mounted in said base portion (1) of said knife holder and is movable in a direction at right angles to a seating surface of said knife or said blade holder.

7. The knife holder according to claim 6, further comprising at least one eccentric shaft (11a, 11b) for coupling pivoting movement of said actuating lever (12a, 12b) with movement of said at least one magnet (7a, 7b).

8. The knife holder according to claim 7, wherein said at least one eccentric shaft (11a, 11b) is guided by a slotted hole (21a, 21b) through said at least one magnet or at least one supporting member (5a, 5b) for said at least one magnet (7a, 7b).

9. The knife holder according to claim 5, wherein said actuating lever (12a, 12b) includes an extension (13a, 13b) that in an fastening position of said knife or blade holder extends at least partially over a cutting edge (29) of said knife or said blade.

10. The knife holder according to claim 9, wherein a first actuating lever (12a) is motion-coupled to two magnets (7a, 7b) and a second actuating lever (12a) is motion-coupled to two additional magnets (7c, 7d).

* * * * *

UNITED STATES PATENT AND TRADEMARK OFFICE
CERTIFICATE OF CORRECTION

PATENT NO. : 5,851,213
DATED : December 22, 1998
INVENTOR(S) : Berleth et al

It is certified that error appears in the above-identified patent and that said Letters Patent is hereby corrected as shown below:

On the cover page,
cancel "[73]   Assignee:     Carl-Zeiss-Stiftung, Germany", and insert -- [73]   Assignee:     MICROM Laborgeräte GmbH, Germany --.

Signed and Sealed this

Twenty-ninth Day of February, 2000

Attest:

Q. TODD DICKINSON

Attesting Officer

Commissioner of Patents and Trademarks